(12) United States Patent
Lin

(10) Patent No.: US 11,986,569 B2
(45) Date of Patent: May 21, 2024

(54) INSTRUMENT STERILIZATION MONITORING SYSTEM AND METHOD

(71) Applicants: Yu-Pin Lin, Hsinchu County (TW); Ching-Feng Lee, Taichung County (TW)

(72) Inventor: Yu-Pin Lin, Hsinchu County (TW)

(73) Assignees: Yu-Pin Lin, Hsinchu County (TW); Ching-Feng Lee, Taichung County (TW)

( * ) Notice: Subject to any disclaimer, the term of this patent is extended or adjusted under 35 U.S.C. 154(b) by 893 days.

(21) Appl. No.: 16/941,547

(22) Filed: Jul. 29, 2020

(65) Prior Publication Data

US 2022/0031899 A1    Feb. 3, 2022

(51) Int. Cl.
*A61L 2/28*    (2006.01)
*G06K 19/06*    (2006.01)
*G06Q 10/0631*    (2023.01)
*G06T 7/00*    (2017.01)

(52) U.S. Cl.
CPC .......... *A61L 2/28* (2013.01); *G06K 19/06037* (2013.01); *G06Q 10/063118* (2013.01); *G06T 7/0004* (2013.01); *A61L 2202/14* (2013.01); *A61L 2202/24* (2013.01)

(58) Field of Classification Search
CPC .... A61L 2/28; A61L 2202/14; A61L 2202/24; G06T 7/0004
See application file for complete search history.

(56) References Cited

U.S. PATENT DOCUMENTS

| | | |
|---|---|---|
| 2003/0187586 A1 | 10/2003 | Katzenmaier et al. |
| 2019/0290796 A1 | 9/2019 | Ma et al. |
| 2020/0023090 A1* | 1/2020 | Axelrod ............... A61L 2/24 |
| 2020/0030476 A1* | 1/2020 | Corsini ............... A61L 2/24 |
| 2020/0038137 A1 | 2/2020 | Russ |
| 2020/0122202 A1* | 4/2020 | Kraus ............... G16H 40/40 |

FOREIGN PATENT DOCUMENTS

WO    WO2015193664 A1    12/2015

* cited by examiner

*Primary Examiner* — Sean E Conley
*Assistant Examiner* — Justin Hwang
(74) *Attorney, Agent, or Firm* — Li & Cai Intellectual Property Office

(57) ABSTRACT

An instrument sterilization monitoring system and an instrument sterilization monitoring method are provided. The instrument sterilization monitoring system includes a server, a sterilization device, and a mobile device. An image capturing module of the mobile device is used to capture image information of a first sterilization device indication device in the sterilization device, image information of a first sterilization device indication label, image information of a second instrument indication device, and image information of a second instrument indication label which are disposed outside an instrument package. The image information is uploaded to the server. The server determines, according to the image information, whether or not the instrument package meets a sterilization standard.

7 Claims, 11 Drawing Sheets

INSTRUMENT STERILIZATION MONITORING SYSTEM AND METHOD

FIELD OF THE DISCLOSURE

The present disclosure relates to an instrument sterilization monitoring system and method, and more particularly to an instrument sterilization monitoring system and method that can reduce the cost of labor.

BACKGROUND OF THE DISCLOSURE

In the medical industry, instrument sterilization is a fundamental and important task. However, most instrument sterilization procedures are manually recorded and determined. Based on the manually recorded content, it is not easy to perform instrument management and usage tracking.

Therefore, how an instrument sterilization monitoring system and an instrument sterilization monitoring method that can reduce the cost of labor can be provided has become a significant subject in the relevant field.

SUMMARY OF THE DISCLOSURE

In response to the above-referenced technical inadequacies, the present disclosure provides an instrument sterilization monitoring system, which includes a server, a sterilization device, and a mobile device; wherein the sterilization device is used to perform a sterilization procedure on a plurality of instruments to be sterilized; the mobile device includes an image capturing module, where the mobile device is used to log in to the server; a first sterilization device indication device is disposed in the sterilization device; at least one of the instruments to be sterilized and a first instrument indication device are placed together in a packaging material to form an instrument package; a second instrument indication device is disposed outside the instrument package; the plurality of instruments to be sterilized is packaged to form a plurality of instrument packages, and the plurality of instrument packages are placed in the sterilization device to perform the sterilization procedure; the first sterilization device indication device includes a first sterilization device indication label, each of the first instrument indication devices includes a first instrument indication label, and each of the second instrument indication devices includes a second instrument indication label; the image capturing module of the mobile device is used to capture image information of the first sterilization device indication device and image information of the corresponding first sterilization device indication label, and the image information of the first sterilization device indication device and the image information of the first sterilization device indication label are transmitted to the server; then, when packaging the first instrument indication devices and the instruments to be sterilized, image information of the first instrument indication devices corresponding to the plurality of instruments to be sterilized and image information of the first instrument indication labels are captured, and the image information of the first instrument indication devices and the image information of the first instrument indication labels are transmitted to the server; and afterwards, the image capturing module of the mobile device is used to capture image information of the second instrument indication devices respectively on the plurality of instrument packages and image information of the corresponding second instrument indication labels, and the image information of each second instrument indication device and the image information of each second instrument indication label are transmitted to the server; after the sterilization device completes the sterilization procedure, image information of the second instrument indication device subjected to the sterilization procedure and image information of the second instrument indication label subjected to the sterilization procedure are captured and the image information of the second instrument indication device and the second instrument indication label that are subjected to the sterilization procedure are transmitted to the server; the image capturing module of the mobile device is used to capture image information of the first sterilization device indication device subjected to the sterilization procedure and image information of the first sterilization device indication label subjected to the sterilization procedure, and the image information of the first sterilization device indication device and the first sterilization device indication label that are subjected to the sterilization procedure are transmitted to the server; and the server determines, according to the image information of the second instrument indication device, the second instrument indication label, the first sterilization device indication device, and the first sterilization device indication label that are subjected to the sterilization procedure, whether or not the instruments to be sterilized meet a sterilization standard.

To solve the foregoing technical problem, one technical solution adopted by the present disclosure is to provide an instrument sterilization monitoring system, which includes a server, a sterilization device, and a mobile device; wherein the sterilization device is used to perform a sterilization procedure on a predetermined quantity of instruments to be sterilized; the mobile device includes an image capturing module, where the mobile device is used to log in to the server with a user account and a user password; a first sterilization device indication device is disposed in the sterilization device; at least one of the instruments to be sterilized and a first instrument indication device are placed together in a packaging material to form an instrument package; a second instrument indication device is disposed outside the instrument package; the plurality of instruments to be sterilized is packaged to form a plurality of instrument packages, and the plurality of instrument packages are placed in the sterilization device to perform the sterilization procedure; the image capturing module of the mobile device is used to capture image information of the first sterilization device indication device and the image information of the first sterilization device indication device is transmitted to the server; when packaging the first instrument indication device and the instruments to be sterilized, image information of the first instrument indication device corresponding to the plurality of instruments to be sterilized are captured, and the image information of the first instrument indication device is transmitted to the server; the image capturing module of the mobile device is used to capture image information of the second instrument indication device disposed outside each instrument package, and the image information of the second instrument indication device is transmitted to the server; after the sterilization device completes the sterilization procedure, image information of the second instrument indication device subjected to the sterilization procedure is captured, and the image information of the second instrument indication device subjected is transmitted to the sterilization procedure to the server; the image capturing module of the mobile device is used to capture image information of the first sterilization device indication device subjected to the sterilization procedure, and the image information of the first sterilization device indication device subjected to the sterilization procedure is transmitted to the server; and the server determines, according to the image information of the second instrument indication device and the first sterilization device indication device that are subjected to the sterilization procedure, whether or not the instruments to be sterilized meet a sterilization standard.

To solve the foregoing technical problem, the other technical solution adopted by the present disclosure is to provide an instrument sterilization monitoring method, which includes: placing a first sterilization device indication device in a sterilization device; capturing image information of the first sterilization device indication device, and transmitting the image information of the first sterilization device indication device to a server; packaging a plurality of instruments to be sterilized and a plurality of first instrument indication devices to form a plurality of instrument packages; capturing image information of each first instrument indication device, and transmitting the image information of the first instrument indication device to the server; disposing a second instrument indication device outside each instrument package; capturing image information of each second instrument indication device, and then transmitting the image information of the second instrument indication device to the server; placing the plurality of instrument packages in the sterilization device; performing a sterilization procedure; after the sterilization device completes the sterilization procedure, capturing image information of the first sterilization device indication device subjected to the sterilization procedure and image information of the second instrument indication device subjected to the sterilization procedure, and transmitting the image information of the first sterilization device indication device and the second instrument indication device that are subjected to the sterilization procedure to the server; and determining by the server, according to the image information of the first sterilization device indication device subjected to the sterilization procedure, whether or not the sterilization device meets a first sterilization standard; and determining by the server, according to the image information of the second instrument indication device subjected to the sterilization procedure, whether or not the instrument package meets a fourth sterilization standard.

One of advantageous effects achieved by the present disclosure lies in that the instrument sterilization monitoring system and method provided by the present disclosure reduce the workload of medical staff. It is only required to use a common mobile phone to photograph and upload images of the instrument packages, and indicators and labels before and after sterilization, to easily monitor whether or not sterilization for the instrument packages in each sterilization procedure succeeds. The instrument sterilization monitoring system and method provided by the present disclosure can further associate the instrument package with patients using the instruments, thereby greatly improving the safety of medical care.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

FIG. 6-1 and FIG. 6-2 are flowcharts of an instrument sterilization monitoring method in a second embodiment of the present disclosure.

DETAILED DESCRIPTION OF THE EXEMPLARY EMBODIMENTS

Figure 1:
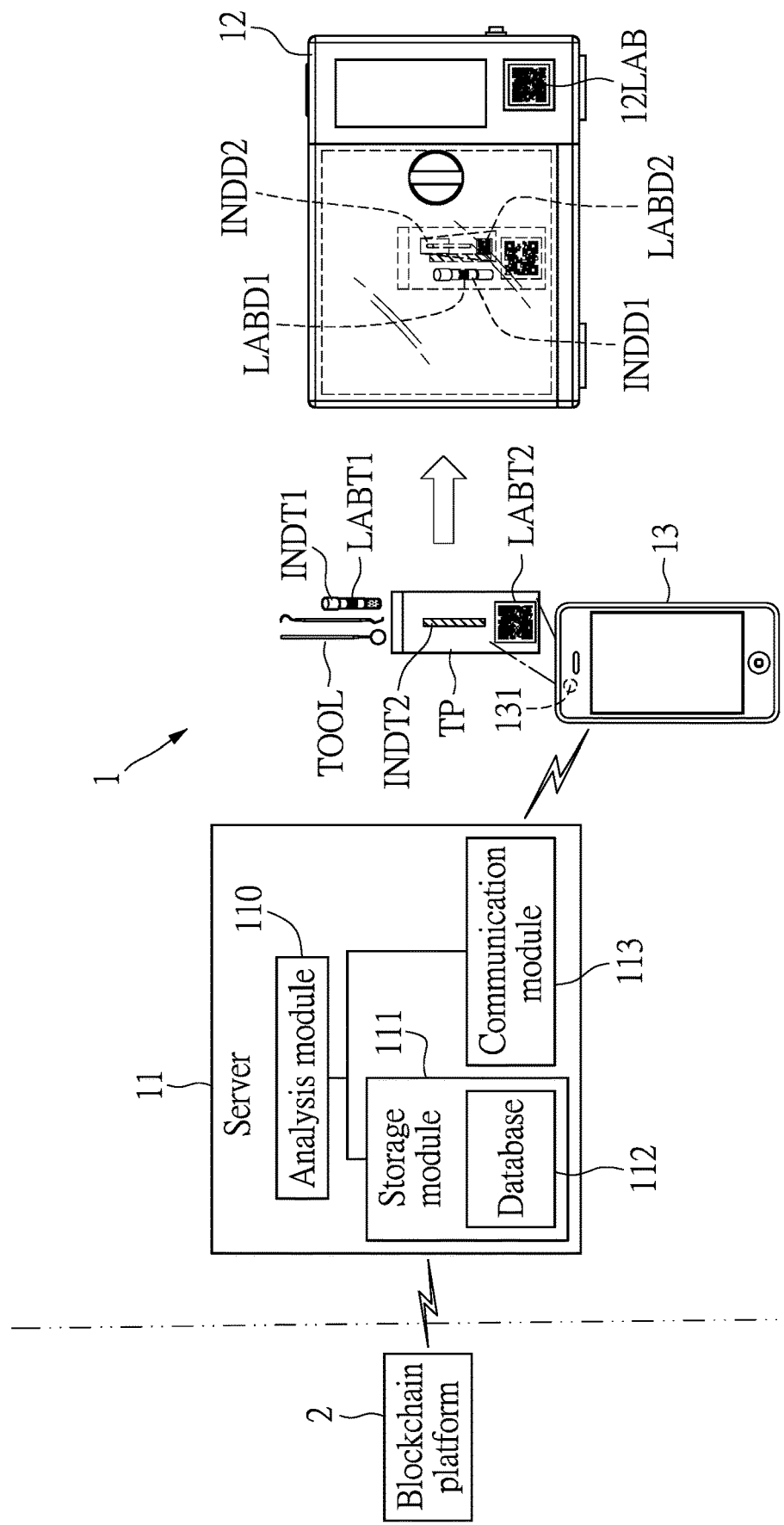
FIG. 1 is a schematic diagram of an instrument sterilization monitoring system in a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The following describes an implementation manner of the present disclosure relating to an "instrument sterilization monitoring system and method" through specific embodiments. Those skilled in the art can easily understand the advantages and effects of the present disclosure from the content disclosed in the specification. The present disclosure can be embodied or applied through other different embodiments. Based on different opinions and applications, the details in the present specification can also be modified and changed without departing from the concept of the present disclosure. In addition, it should be stated first that the accompanying drawings of the present disclosure are merely for brief illustration and not drawn according to actual dimensions. The following embodiments will further explain the related technical content of the present disclosure, but the disclosed content is not intended to limit the scope of protection of the present disclosure. In addition, the term "or" as used herein shall, according to the actual situation, include any one or a combination of more of the associated listed items.

First Embodiment

Figure 2A:
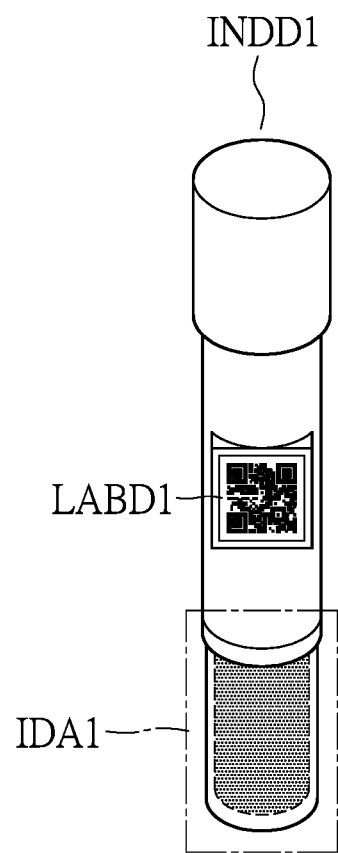
FIGS. 2A, 2B, and 2C are different schematic diagrams of a first sterilization device indication device of the instrument sterilization monitoring system in FIG. 1.
Figure 2B:
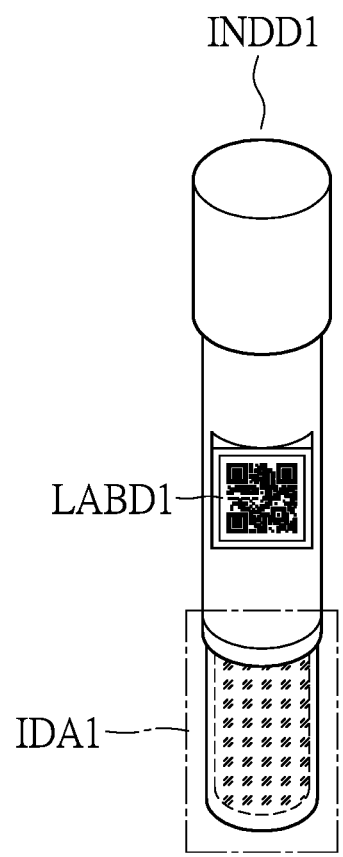
Figure 2C:
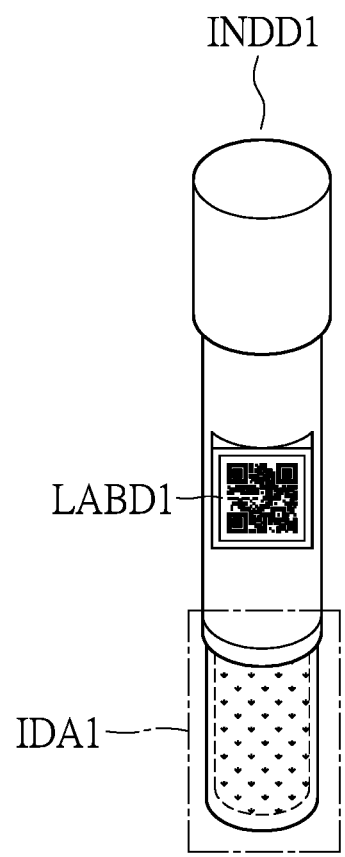
Figure 3A:
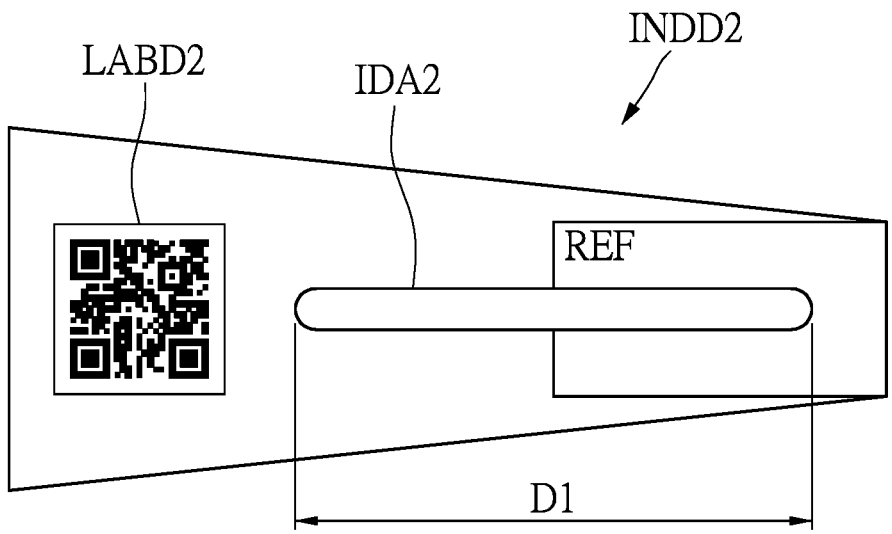
FIG. 3A is a schematic diagram of a second sterilization device indication device of the instrument sterilization monitoring system in FIG. 1.
Figure 3B:
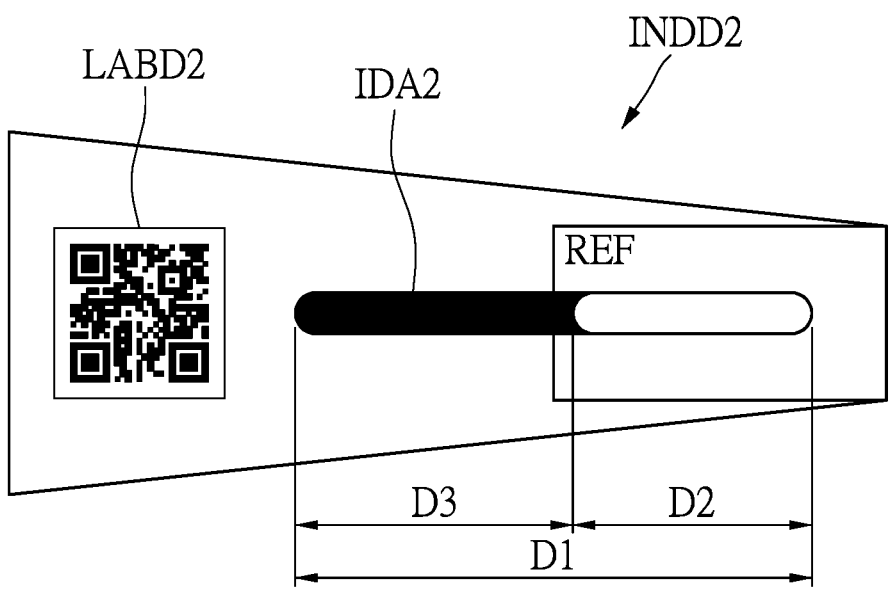
FIGS. 3B, 3C, and 3D are schematic diagrams showing that the second sterilization device indication device in FIG. 3A meets a sterilization standard.
Figure 3C:
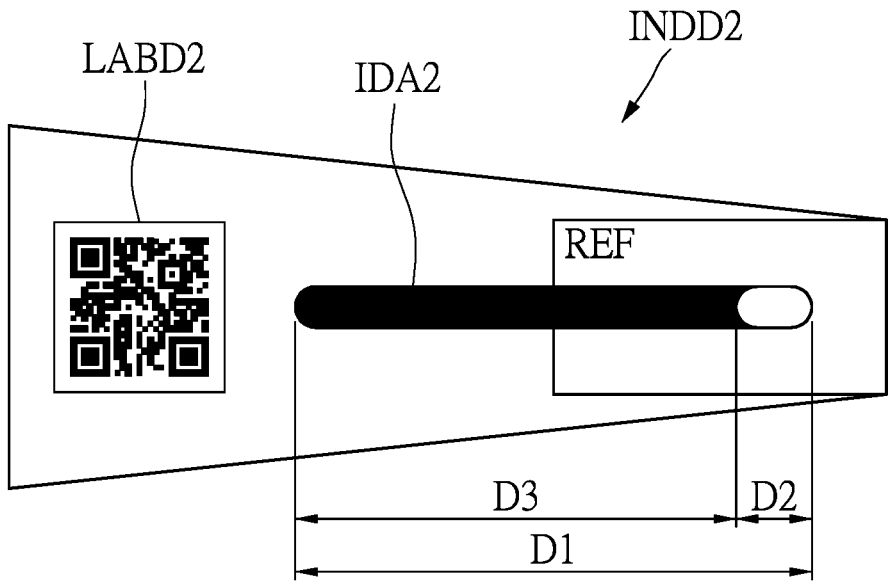
Figure 3D:
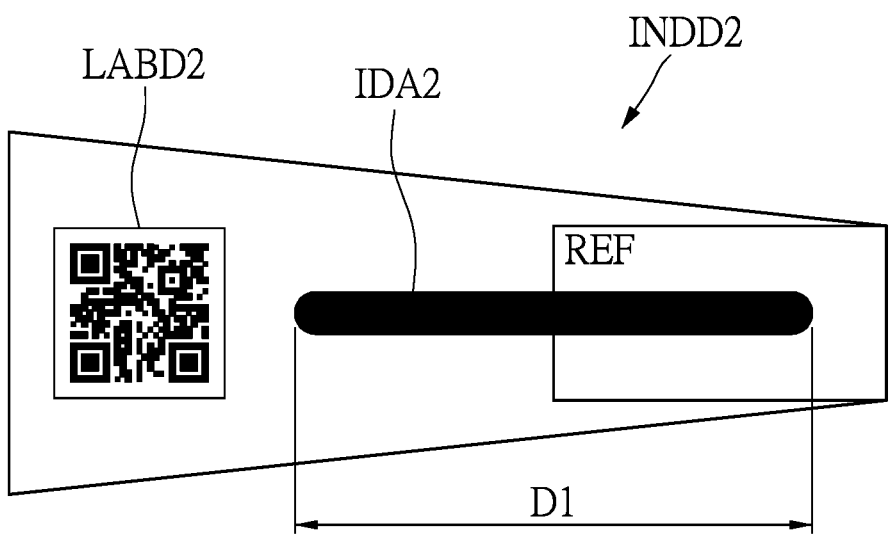
Figure 3E:
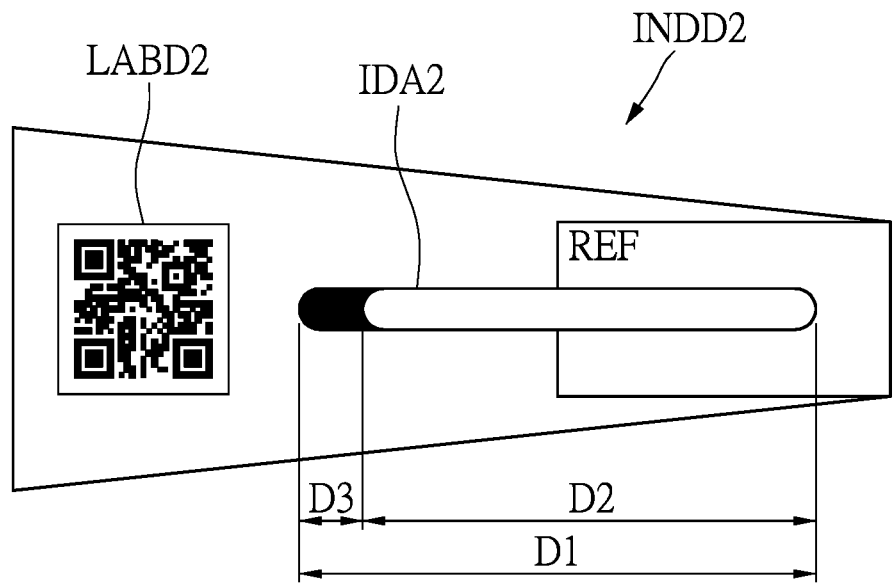
FIGS. 3E and 3F are schematic diagrams showing that the second sterilization device indication device in FIG. 3A fails to meet the sterilization standard.
Figure 3F:
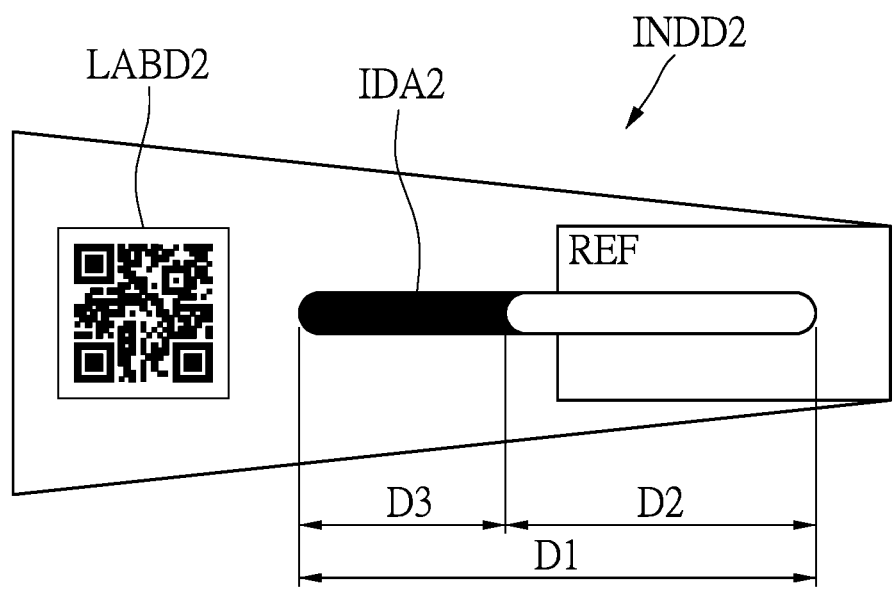

Referring to FIGS. 1, 2A, 2B, 2C, 3A, 3B, 3C, 3D, 3E, and 3F, FIG. 1 is a schematic diagram of an instrument sterilization monitoring system in a first embodiment of the present disclosure. FIGS. 2A, 2B, and 2C are different schematic diagrams of a first sterilization device indication device of the instrument sterilization monitoring system in FIG. 1. FIG. 3A is a schematic diagram of a second sterilization device indication device of the instrument sterilization monitoring system in FIG. 1. FIGS. 3B, 3C, and 3D are schematic diagrams showing that the second sterilization device indication device in FIG. 3A meets a sterilization standard. FIGS. 3E and 3F are schematic diagrams showing that the second sterilization device indication device in FIG. 3A fails to meet the sterilization standard.

In this embodiment, the instrument sterilization monitoring system 1 includes a server 11, a sterilization device 12, and a mobile device 13. The server 11 includes an analysis module 110, a storage module 111, a database 112, and a communication module 113. The analysis module 110 is connected to the storage module 111, the database 112, and the communication module 113. The server 11 is communicatively connected to the mobile device 13 via the communication module 113, and is communicatively connected to a blockchain platform 2 via the communication module 113.

The sterilization device 12 is an autoclave which is a high-temperature, high-pressure sterilization device with timer function. Having a certain capacity, the sterilization device 12 needs to meet predetermined requirements in terms of a sterilization procedure, temperature, and pressure, so as to reach a sterilization standard. The sterilization device 12 can sterilize only a predetermined quantity of instruments each time, and may fail to reach the sterilization standard if sterilizing instruments are more than the predetermined quantity. In this embodiment, two sterilization standards: a first sterilization standard and a second sterilization standard are set for the sterilization device 12. A detection result regarding the second sterilization standard can be immediately known, while a biological culture for a certain time needs to be carried out before determining whether or not the first sterilization standard is completely met. In addition, a third sterilization standard is set for a sterilization status of instruments TOOL, and a fourth sterilization standard is set for a sterilization status of an instrument package TP. Each of the foregoing sterilization standards are respectively detected by using an indication device.

An application program corresponding to the instrument sterilization monitoring system 1 is set in the mobile device 13. The mobile device 13 has a communication function and can be communicatively connected to the server 11. The mobile device 13 includes an image capturing module 131. In this embodiment, the mobile device 13 is a smart phone, a tablet computer, or a wearable electronic device. In other words, a user can use a camera module of the mobile device 13 to capture images of various indication devices in this embodiment, thus easily completing tracking and verification of instrument sterilization. In this embodiment, instruments to be sterilized are mostly medical instruments, such as a dental instrument, surgical instrument, operative instrument, or the like. Moreover, the user can use the mobile device 13 to log in to the server 11 with a user account and a user password. While the user uses the mobile device 13 to log in to the server 11, the mobile device 13 provides position information to the server 11. The server 11 determines a login site of the user according to a login signal from the user. Because the sterilization device 12 is used mostly in hospitals, clinics, or certified providers of medical supplies and services, the login site of the user and a site where image information in a subsequent sterilization procedure is uploaded are also recorded together by the server 11. In this embodiment, the sterilization device 12 includes a sterilization device label 12LAB which is disposed outside the sterilization device 12. When using the sterilization device 12 to perform the sterilization procedure, the user needs to use the image capturing module 131 of the mobile device 13 to capture image information of the sterilization device label 12LAB, and transmits the image information of the sterilization device label 12LAB to the server 11 for recording.

Before the sterilization procedure, the instruments TOOL are first subjected to procedures such as immersion in disinfectant, cleaning, drying, and the like. The instruments TOOL need to be cleaned before the sterilization procedure.

Referring to FIGS. 2A, 2B, and 2C, after being cleaned, the instruments TOOL are first packaged. The user may select a packaging material and a corresponding instrument TOOL by tapping on the application program in the mobile device 13. Then the application program in the mobile device 13 generates a first sterilization device indication label LABD1, a second sterilization device indication label LABD2, a first instrument indication label LABT1, and a second instrument indication label LABT2 according to the packaging material and the instrument TOOL selected by the user. In this embodiment, before the sterilization procedure, a first sterilization device indication device INDD1 and a second sterilization device indication device INDD2 are required to be placed into the sterilization device 12. The first sterilization device indication device INDD1 is used to determine whether or not the sterilization device 12 reaches a first sterilization standard after completion of a current sterilization procedure. The second sterilization device indication device INDD2 is used to determine whether or not the sterilization device 12 reaches a second sterilization standard after completion of the current sterilization procedure. In this embodiment, the first sterilization device indication device INDD1 is a bottled indicator having a biological culture and interpretation system, for example, the 3M™ Attest™ Biological Indicator (1261P or 1262P). The first sterilization device indication device INDD1 is mainly characterized by having a particular color, and can be used to determine, according to its color change, whether sterilization succeeds or fails after the sterilization procedure. In this embodiment, an initial color of the first sterilization device indication device INDD1 is purple. Colors of the first sterilization device indication device INDD1 that indicate sterilization failure and sterilization success are respectively yellow and blue.

Referring to FIGS. 3A, 3B, 3C, 3D, 3E and 3F, the second sterilization device indication device INDD2 is an integrated chemical indicator, for example, the 3M™ Comply™ (Steri Gage) Steam Chemical Indicator (1243B). In this embodiment, the second sterilization device indication device INDD2 is a card-type indication device, and is used to determine whether or not sterilization succeeds in an environment in the sterilization device 12. A bar-shaped indication box is on the second sterilization device indication device INDD2. When sterilization succeeds, the bar-shaped indication box changes in color, that is, has a first color and a second color. The first color is an initial color of the bar-shaped indication box, and the second color is a color of the bar-shaped indication box after the change. In this embodiment, the first color is gray and the second color is black. When sterilization succeeds, a length of the second color exceeds a predetermined distance Immediately after the sterilization procedure, the second sterilization device indication device INDD2 determines whether or not a second sterilization standard is met in an environment of the sterilization procedure in the sterilization device 12.

Figure 4A:
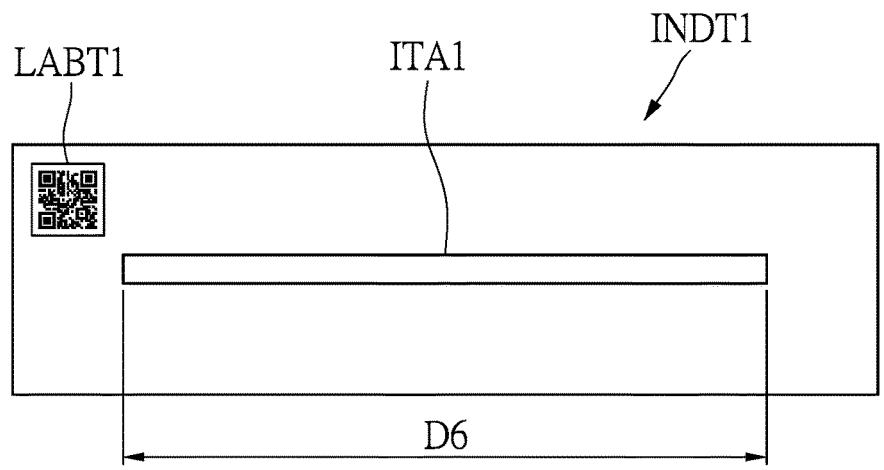
FIG. 4A is a schematic diagram of a first instrument indication device of the instrument sterilization monitoring system in FIG. 1.
Figure 4B:
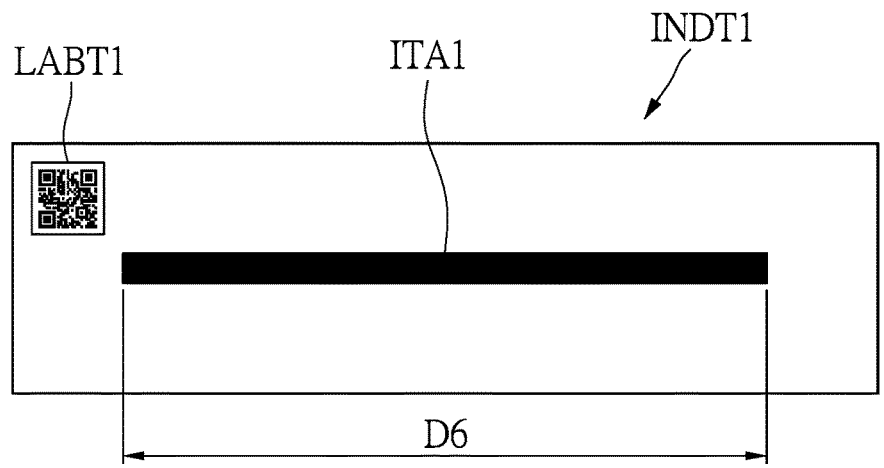
FIG. 4B is a schematic diagram showing that the first instrument indication device of the instrument sterilization monitoring system in FIG. 1 succeeds in sterilization.
Figure 4C:
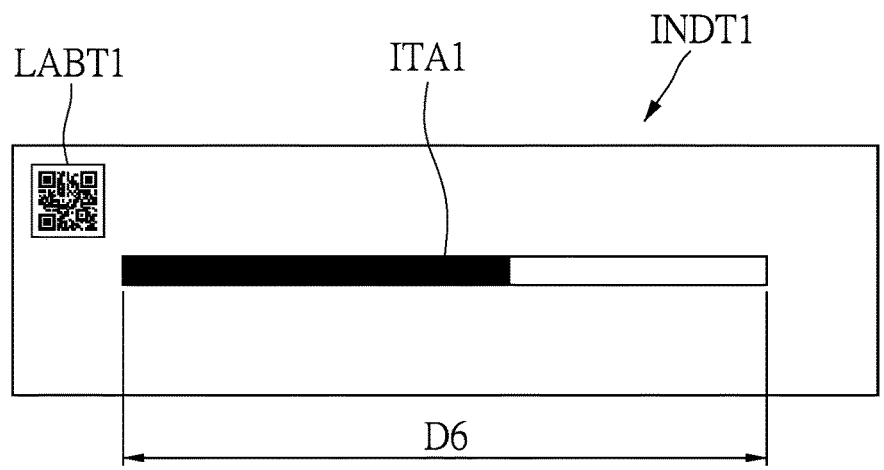
FIGS. 4C, 4D, 4E, 4F, 4G, and 4H are schematic diagrams showing that the first instrument indication device of the instrument sterilization monitoring system in FIG. 1 fails in sterilization.
Figure 4D:
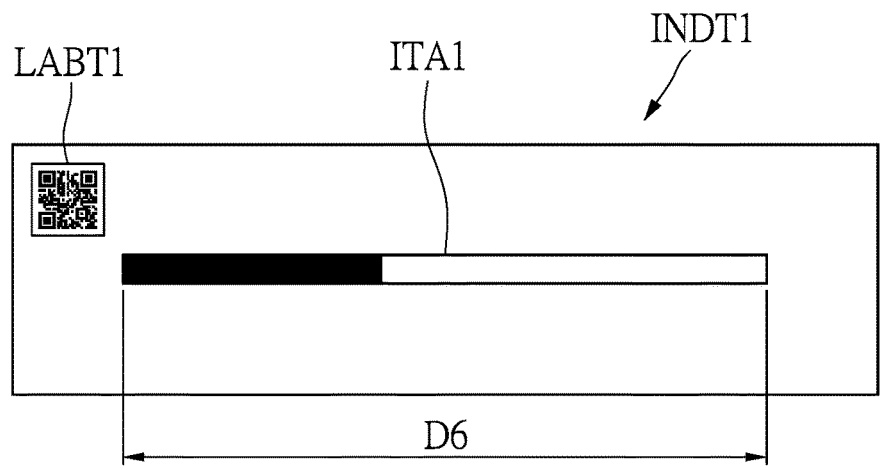
Figure 4E:
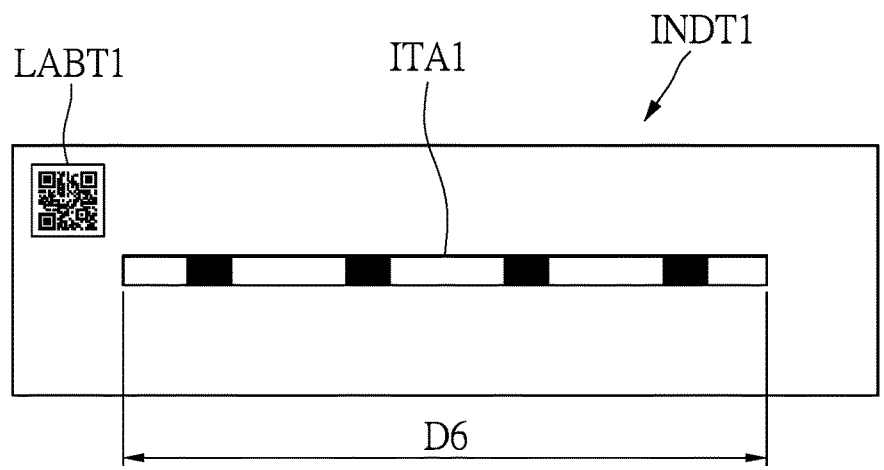
Figure 4F:
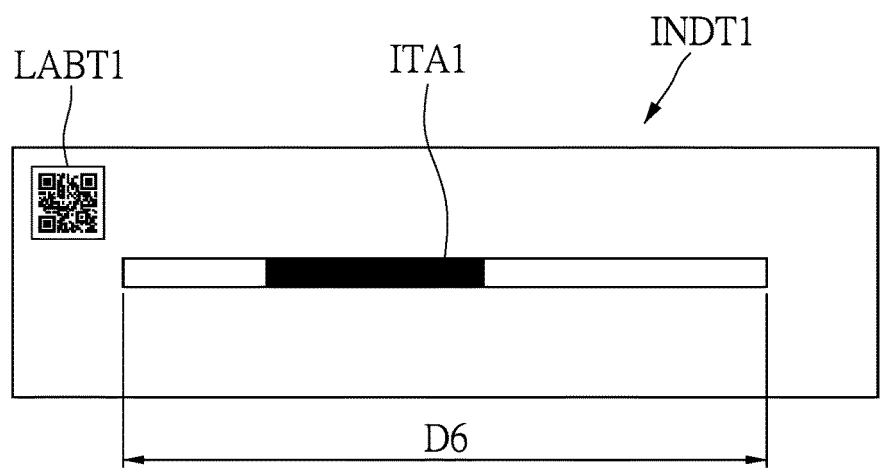
Figure 4G:
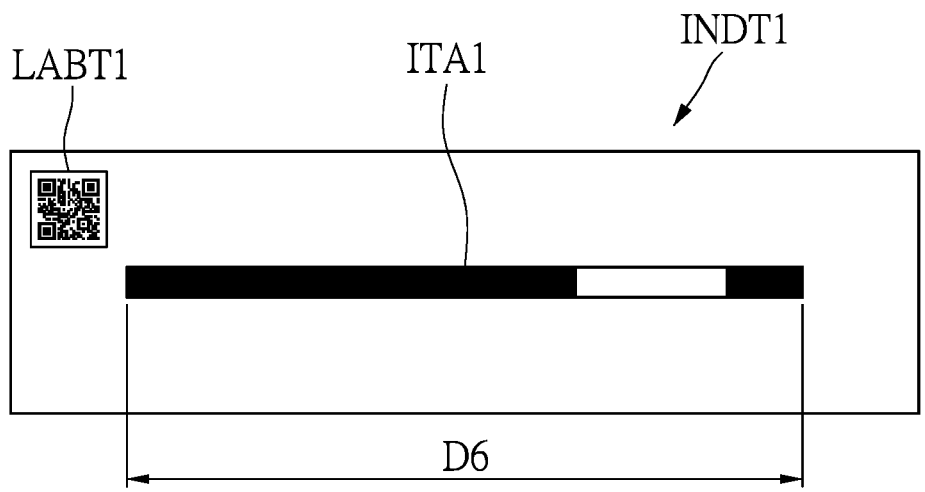
Figure 4H:
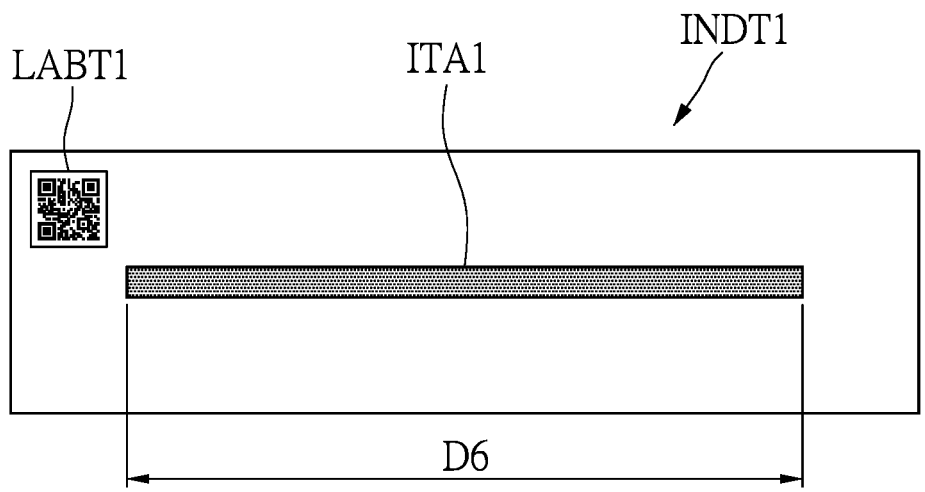
Figure 5A:
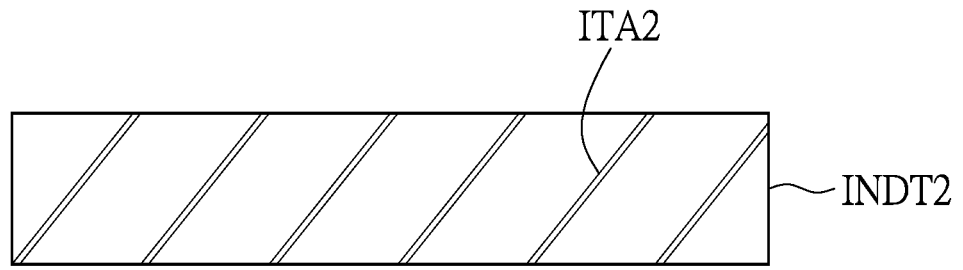
FIGS. 5A and 5B are schematic diagrams of a second instrument indication device of the instrument sterilization monitoring system in FIG. 1.
Figure 5B:
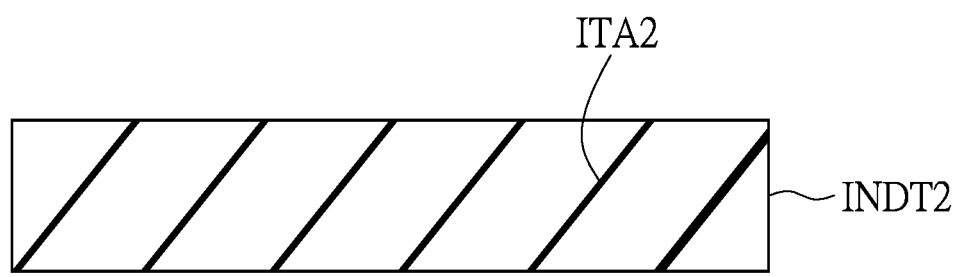

Referring to FIGS. 1, 4A, 4B, 4C, 4D, 4E, 4F, 4G, 4H, 5A, and 5B, FIG. 4A is a schematic diagram of a first instrument indication device of the instrument sterilization monitoring system in FIG. 1. FIG. 4B is a schematic diagram showing that the first instrument indication device of the instrument sterilization monitoring system in FIG. 1 succeeds in sterilization. FIGS. 4C, 4D, 4E, 4F, 4G, and 4H are schematic diagrams showing that the first instrument indication device of the instrument sterilization monitoring system in FIG. 1 fails in sterilization. FIGS. 5A and 5B are schematic diagrams of a second instrument indication device of the instrument sterilization monitoring system in FIG. 1.

The instrument TOOL to be sterilized and the first instrument indication device INDT1 are packaged together to form an instrument package TP. A second instrument indication device INDT2 is disposed outside the instrument package TP. The second instrument indication device INDT2 in this embodiment is an indication device of an adhesive tape type, for example, the 3M™ Comply™ Steam Chemical Indicator (1322-12 mm, lead-free). When sterilization succeeds, predetermined stripes on the second instrument indication device INDT2 change in color.

In this embodiment, the first sterilization device indication label LABD1, the second sterilization device indication label LABD2, the first instrument indication label LABT1, and the second instrument indication label LABT2 are disposed respectively at one side of the first sterilization device indication device INDD1, one side of the second sterilization device indication device INDD2, one side of the first instrument indication device INDT1, and one side of the second instrument indication device INDT2. The first sterilization device indication label LABD1, the second sterilization device indication label LABD2, the first instrument indication label LABT1, and the second instrument indication label LABT2 are used as data recording bases respectively for the first sterilization device indication device INDD1, the second sterilization device indication device INDD2, the first instrument indication device INDT1, and the second instrument indication device INDT2.

The user may use the mobile device 13 to capture image information of the first sterilization device indication device INDD1, image information of the second sterilization device indication device INDD2, image information of the first instrument indication device INDT1, and image information of the second instrument indication device INDT2, and transmit the image information of the first sterilization device indication device INDD1, the image information of the second sterilization device indication device INDD2, the image information of the first instrument indication device INDT1, and the image information of the second instrument indication device INDT2 to the server 11 for storage, recording, and analysis.

Further, the user may also use the image capturing module 131 of the mobile device 13 to capture image information of the first sterilization device indication label LABD1, image information of the second sterilization device indication label LABD2, image information of the first instrument indication label LABT1, and image information of the second instrument indication label LABT2, and transmit the image information of the first sterilization device indication label LABD1, the image information of the second sterilization device indication label LABD2, the image information of the first instrument indication label LABT1, and the image information of the second instrument indication label LABT2 to the server 11 for storage, recording, and analysis.

In other embodiments, the user may transmit only the image information of the first sterilization device indication device INDD1, the image information of the first instrument indication device INDT1, and the image information of the second instrument indication device INDT2 to the server 11 for storage, recording, and analysis.

After placing a plurality of instrument packages TP in the sterilization device 12, the user may select different sterilization procedures for the sterilization device 12 according to different types of instruments. In addition, the user may also use the image capturing module 131 of the mobile device 13 to capture display information regarding the sterilization procedures of the sterilization device 12, and transmit the display information to the server 11 for storage and recording.

After the sterilization device 12 completes the sterilization procedure, the user opens the sterilization device 12 to take out the plurality of instrument packages TP subjected to the sterilization procedure.

In this case, the user may use the image capturing module 131 of the mobile device 13 to capture image information of the first sterilization device indication device INDD1 subjected to the sterilization procedure, image information of the second sterilization device indication device INDD2 subjected to the sterilization procedure, image information of the second instrument indication device INDT2 which is disposed outside the instrument package TP and subjected to the sterilization procedure, and image information of the second instrument indication label LABT2 which is disposed outside the instrument package TP and subjected to the sterilization procedure, and transmit the image information of the first sterilization device indication device, the second sterilization device indication device, the second instrument indication device, and the second instrument indication label that are subjected to the sterilization procedure to the server 11.

Afterwards, the server 11 determines, according to the image information of the second instrument indication device subjected to the sterilization procedure, the image information of the second instrument indication label subjected to the sterilization procedure, the image information of the first sterilization device indication device subjected to the sterilization procedure, the image information of the second sterilization device indication device subjected to the sterilization procedure, and the image information of the first sterilization device indication label subjected to the sterilization procedure, whether or not the instrument TOOL to be sterilized meets a sterilization standard. That is, the server 11 performs an image recognition procedure on the image information of the second instrument indication device and the second instrument indication label that are subjected to the sterilization procedure, to determine whether or not a sterilization indication area on the second instrument indication device INDT2 disposed outside the instrument package TP meets a fourth sterilization standard after the sterilization procedure. The server 11 performs image recognition on the image information of the first sterilization device indication device and the second sterilization device indication device that are subjected to the sterilization procedure. The server recognizes information of an elongated bottle-shaped object in the image information of the first sterilization device indication device subjected to the sterilization procedure, and further analyzes color information of a first indication area in the information of the elongated bottle-shaped object. Then the server 11 recognizes a bar-shaped indication area in the image information of the second sterilization device indication device, to determine whether or not a length of a second color is longer than a length of a first color.

The image information of the first sterilization device indication label, the image information of the second sterilization device indication label, the image information of the first instrument indication label, and the image information of the second instrument indication label may be one-dimensional bar code, two-dimensional bar code, multi-dimensional bar code, or radio frequency identification code (RFID). The image information of the first sterilization device indication label, the image information of the first instrument indication label, and the image information of the second instrument indication label are mainly serial numbers or running numbers after decoding, so as to be associated with the image information of the first sterilization device indication device, the image information of the second sterilization device indication label, the image information of the first instrument indication device, and the image information of the second instrument indication device before and after sterilization, and to be recorded.

The server 11 also performs an image recognition procedure on the image information of the second instrument indication device and the second instrument indication label that are subjected to the sterilization procedure. A plurality of diagonal stripes is provided on a surface of the second instrument indication device INDT2. When the instrument package TP meets the fourth sterilization standard after the sterilization procedure, the plurality of diagonal stripes on the second instrument indication device INDT2 changes in color.

After the instrument package TP subjected to the sterilization procedure is unpacked, the user uses the image capturing module 131 of the mobile device 13 to capture image information of the first instrument indication device INDT1 subjected to the sterilization procedure and image information of the first instrument indication label LABT1 subjected to the sterilization procedure, and transmits the image information of the first instrument indication device INDT1 and the first instrument indication label LABT1 that are subjected to the sterilization procedure to the server 11.

The server 11 performs image recognition on the image information of the first instrument indication device and the image information of the first instrument indication label, to determine whether or not instruments TOOL in the instrument package TP meet a third sterilization standard after the sterilization procedure.

In this embodiment, the first sterilization device indication device INDD1, the second sterilization device indication device INDD2, the first instrument indication device INDT1, and the second instrument indication device INDT2 respectively include a first sterilization device indication area IDA1, a second sterilization device indication area IDA2, a first instrument indication area ITA1, and a second instrument indication area ITA2.

The server 11 determines, according to color change information of the first sterilization device indication area IDA1 and color change and length information of the second sterilization device indication area IDA2 in the image information of the first sterilization device indication device, whether or not the sterilization device 12 meets a first sterilization standard and a second sterilization standard.

The server 11 determines, according to a color change of the second instrument indication area ITA2 of the second instrument indication device INDT2, whether or not the instrument package TP meets a fourth sterilization standard.

In this embodiment, when the first sterilization device indication device INDD1 fails to meet the first sterilization standard or the second sterilization device indication device INDD2 fails to meet the second sterilization standard, all the instrument packages TP after the current sterilization procedure are required to be subjected to the sterilization procedure again, and it is unsuitable to use any of the instrument packages TP after the current sterilization procedure. When the second instrument indication device INDT2 disposed outside the instrument package TP fails to meet the fourth sterilization standard, the instruments TOOL in the instrument package TP are required to be re-packaged and subjected to another sterilization procedure. Likewise, when the first instrument indication device INDT1 fails to meet the third sterilization standard after the instrument package TP is unpacked, the instruments TOOL in the instrument package TP cannot be used, and are required to be re-packaged and subjected to another sterilization procedure. Moreover, an instrument package TP failing to comply with the sterilization procedure or an instrument TOOL failing to comply with the sterilization procedure is required to be abandoned by using the application program in the mobile device 13, so as to implement the another sterilization procedure.

Referring to FIGS. 4A, 4B, 4C, 4D, 4E, 4F, 4G, and 4H, the first instrument indication device INDT1 is also a card-type indication device, and the first instrument indication area ITA1 of the first instrument indication device INDT1 defines an indicator coating range. Before the sterilization procedure, a color of the first instrument indication area ITA1 is white (as shown in FIG. 4A), after the sterilization procedure, the color of the first instrument indication area ITA1 is changed to black (as shown in FIG. 4B). The first instrument indication area ITA1 has a total length of D6. After the sterilization procedure, if sterilization succeeds, a black color emerges in the first instrument indication area ITA1, and moreover extends to the total length D6. Only in this case, the first instrument indication device INDT1 meets the third sterilization standard. In addition, if a length of black segments shown in FIGS. 4C, 4D, 4E, 4F, and 4G are all shorter than the total length D6 of the first instrument indication area ITA1, or the black color is presented segmentally, the first instrument indication device INDT1 fails to meet the third sterilization standard in either of the two cases. Alternatively, as shown in FIG. 4H, although the first instrument indication area ITA1 has a color change, the color is neither black nor dark gray. In this case, the first instrument indication device INDT1 also fails to meet the third sterilization standard.

Moreover, when the user uploads all the image information to the server 11 by using the application program in the mobile device 13, the server 11 may record upload times of all the image information and GPS position information of the mobile device 13, further analyze time information of metadata of each piece of image information, and compare the analyzed time information with the upload time, so as to guarantee that capturing time of the image information is close to the upload time. In addition, the server 11 may monitor instrument use by the user according to a time interval during which the sterilization device 12 performs the sterilization procedure each time, and according to the quantity of the instrument packages TP and a related record (from the second instrument indication label outside a package). Further, when the server 11 recognizes the first instrument indication area ITA1 of the first instrument indication device INDT1, a length of a color change zone in the first instrument indication area ITA1 is necessarily equal to the total length D6, and a color variation of the first instrument indication area ITA1 is necessarily less than a preset grayscale value (intensity). For example, based on a 256-level grayscale chart (0 to 255), a grayscale value of the first instrument indication area ITA1 may be set to be less than or equal to a 50 grayscale value, so that the third sterilization standard can be met. Moreover, if the preset grayscale value at which the third sterilization standard can be reached is determined to be excessively large, a deviation from an actual sterilization status easily occurs.

For example, if it is required to perform a sterilization procedure on twenty instrument packages TP at a current time, the server 11 records these twenty instrument packages TP subjected to the current sterilization procedure. After the twenty instrument packages TP are unpacked and used, they are associated with medical records of patients or re-sterilized. Afterwards, the server 11 provides a comprehensive sterilization history report on procedures of packaging and sterilization, and usage of the twenty instrument packages TP to the user. In addition, the server 11 further transmits the comprehensive sterilization history report to a blockchain platform. The server 11 may also make association between packaging of each individual instrument package TP, the corresponding sterilization procedure, and data regarding patients using the instruments of the package, and may further perform instrument tracking and adjust the sterilization procedure of the sterilization device 12 according to history information of this individual instrument package TP.

In other embodiments, a pressure value, temperature value, sterilization time, and other parameters of the sterilization device 12 may also be transmitted to the server 11 for storage and recording so as to form a correlation with each sterilization procedure. The server 11 may further determine, according to a sterilization success rate of each sterilization procedure for the instrument package TP, whether or not to calibrate the sterilization device 12. When the sterilization success rate of the sterilization procedure for the instrument package TP is dramatically reduced, the server 11 may send calibration suggestion information to the mobile device 13 of the user.

Second Embodiment

Figures 1, 6:
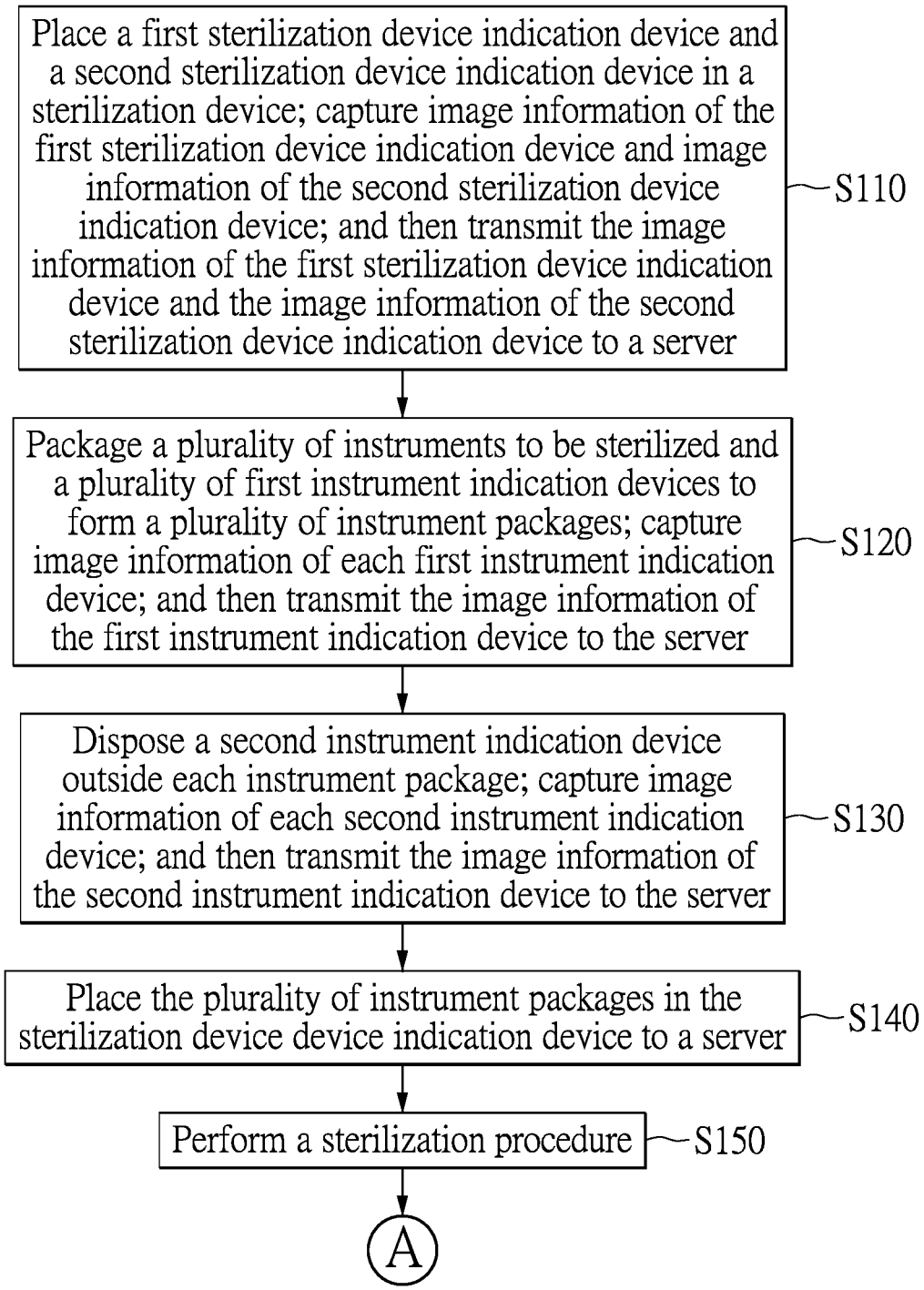
Figures 2, 6:
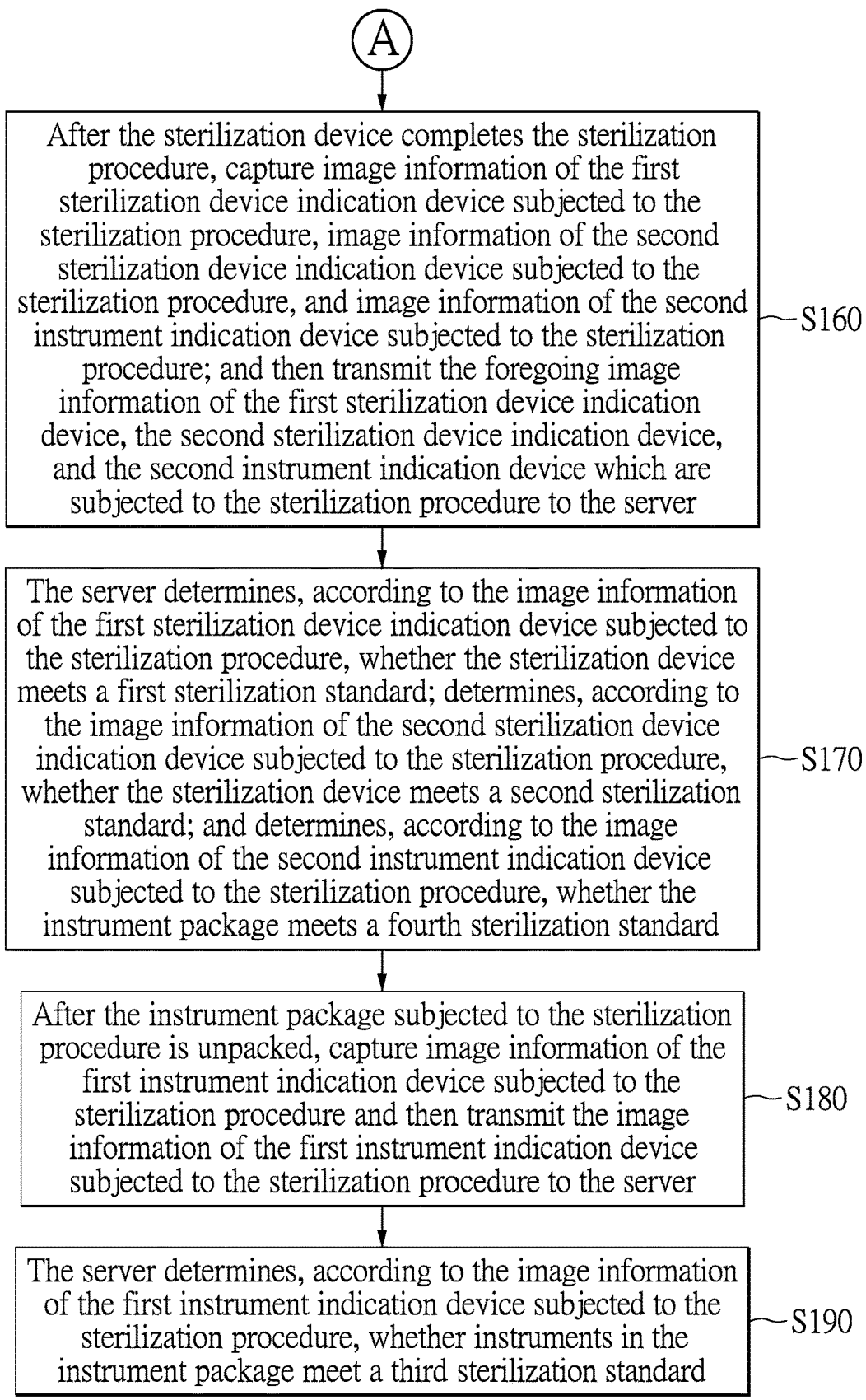

Reference is made to FIG. 6-1 and FIG. 6-2, which are flowcharts of an instrument sterilization monitoring method in a second embodiment of the present disclosure.

The instrument sterilization monitoring method in this embodiment includes the following steps:

A first sterilization device indication device and a second sterilization device indication device are placed in a sterilization device, and image information of the first sterilization device indication device and image information of the second sterilization device indication device are captured and then transmitted to a server (step S110).

A plurality of instruments to be sterilized and a plurality of first instrument indication devices are packaged to form a plurality of instrument packages, and image information of each of the first instrument indication devices is captured and then transmitted to the server (step S120).

A second instrument indication device is disposed outside each instrument package, and image information of each second instrument indication device is captured and then transmitted to the server (step S130).

The plurality of instrument packages is placed in the sterilization device (step S140).

A sterilization procedure is performed (step S150).

After the sterilization device completes the sterilization procedure, image information of the first sterilization device indication device subjected to the sterilization procedure, image information of the second sterilization device indication device subjected to the sterilization procedure, and image information of the second instrument indication device subjected to the sterilization procedure are captured and then transmitted to the server (step S160).

The server determines, according to the image information of the first sterilization device indication device and the second sterilization device indication device that are subjected to the sterilization procedure, whether or not the sterilization device meets a first sterilization standard and a second sterilization standard. The server determines, according to the image information of the second instrument indication device subjected to the sterilization procedure, whether or not the instrument package meets a fourth sterilization standard (step S170).

The instrument sterilization monitoring method further includes the following steps:

After the instrument package subjected to the sterilization procedure is unpacked, image information of the first instrument indication device subjected to the sterilization procedure is captured and transmitted to the server (step S180).

The server determines, according to the image information of the first instrument indication device subjected to the sterilization procedure, whether or not instruments in the instrument package meet a third sterilization standard (step S190).

In steps S110, S120, and S130, an instrument sterilization monitoring system 1 in this embodiment includes a server 11, a sterilization device 12, and a mobile device 13.

The sterilization device 12 is an autoclave which is a high-temperature, high-pressure sterilization device with timer function. Having a certain capacity, the sterilization device 12 needs to meet predetermined requirements in terms of a sterilization procedure, temperature, and pressure, so as to reach a sterilization standard. The sterilization device 12 can sterilize only a predetermined quantity of instruments each time, and may fail to reach the sterilization standard if the sterilizing instruments are more than the predetermined quantity.

An application program corresponding to the instrument sterilization monitoring system 1 is set in the mobile device 13. The mobile device 13 has a communication function and can be communicatively connected to the server 11. The mobile device 13 includes an image capturing module 131. In this embodiment, the mobile device 13 is a smart phone, a tablet computer, or a wearable electronic device. In other words, a user can use a camera module of the mobile device 13 to capture images of various indication devices in this embodiment, thus easily completing tracking and verification of instrument sterilization. In this embodiment, instruments to be sterilized are mostly medical instruments, such as a dental instrument, surgical instrument, operative instrument, or the like. Moreover, the user can use the mobile device 13 to log in to the server 11 with a user account and a user password. While the user uses the mobile device 13 to log in to the server 11, the mobile device 13 provides position information to the server 11. The server 11 determines a login site of the user according to a login signal from the user. Because the sterilization device 12 is used mostly in hospitals, clinics, or certified providers of medical supplies and services, the login site of the user and a site where image information in a subsequent sterilization procedure is uploaded are also recorded together by the server 11.

Before the sterilization procedure, instruments TOOL are first subjected to procedures such as immersion in disinfectant, cleaning, drying, and the like. The instruments TOOL need to be cleaned before the sterilization procedure. After being cleaned, the instruments TOOL are first packaged. The user may select a packaging material and a corresponding instrument TOOL by tapping on the application program in the mobile device 13. Then the application program in the mobile device 13 generates an instrument label according to the packaging material and the instrument TOOL selected by the user. In this embodiment, before the sterilization procedure, a first sterilization device indication device INDD1 and a second sterilization device indication device INDD2 are required to be placed into the sterilization device 12. The first sterilization device indication device INDD1 is used to determine whether or not the sterilization device 12 reaches a sterilization standard after completion of the current sterilization procedure. In this embodiment, the first sterilization device indication device INDD1 is a bottled indicator having a biological culture and interpretation system, for example, the 3M™ Attest™ Biological Indicator (1261P or 1262P). The first sterilization device indication device INDD1 is mainly characterized by having a particular color, and can be used to determine, according to its color change, whether sterilization succeeds or fails after the sterilization procedure. In this embodiment, an initial color of the first sterilization device indication device INDD1 is purple. Colors of the first sterilization device indication device INDD1 that indicate sterilization failure and sterilization success are respectively yellow and blue. The second sterilization device indication device INDD2 is an integrated chemical indicator, for example, the 3M™ Comply™ (Steri Gage) Steam Chemical Indicator (1243B). In this embodiment, the second sterilization device indication device INDD2 is a card-type indication device, and is used to determine whether or not sterilization succeeds in an environment in the sterilization device 12. A bar-shaped indication box is on the second sterilization device indication device INDD2. When sterilization succeeds, the bar-shaped indication box changes in color, that is, has a first color and a second color. The first color is an initial color of the bar-shaped indication box, and the second color is a color of the bar-shaped indication box after the change. In this embodiment, the first color is gray and the second color is black. When sterilization succeeds, a length of the second color exceeds a predetermined distance.

Immediately after the sterilization procedure, the second sterilization device indication device INDD2 determines whether or not a second sterilization standard is met in an environment of the sterilization procedure in the sterilization device 12. In this embodiment, a second indication area of the second sterilization device indication device INDD2 has a first predetermined color before the sterilization procedure, and has a second predetermined color after the sterilization procedure. When a length of the second predetermined color is longer than a length of the first predetermined color, it indicates that the second sterilization standard is met, and when the length of the second predetermined color is shorter than the length of the first predetermined color, it indicates that the second sterilization standard is not met.

When packaging an instrument TOOL to be sterilized, a first instrument indication device INDT1 and the instrument TOOL to be sterilized are packaged together. After the instrument TOOL to be sterilized and the first instrument indication device INDT1 are packaged together, an instrument package TP is formed. A second instrument indication device INDT2 is disposed outside the instrument package TP. The second instrument indication device INDT2 in this embodiment is an indication device of an adhesive tape type, for example, the 3M™ Comply™ Steam Chemical Indicator (1322-12 mm, lead-free). When sterilization succeeds, predetermined stripes on the second instrument indication device INDT2 change in color.

In this embodiment, the first sterilization device indication label LABD1, the first instrument indication label LABT1, and the second instrument indication label LABT2 are disposed respectively at one side of the first sterilization device indication device INDD1, one side of the first instrument indication device INDT1, and one side of the second instrument indication device INDT2. The first sterilization device indication label LABD1, the first instrument indication label LABT1, and the second instrument indication label LABT2 are used as data recording bases respectively for the first sterilization device indication device INDD1, the first instrument indication device INDT1, and the second instrument indication device INDT2.

The user may use the mobile device 13 to capture image information of the first sterilization device indication device INDD1, image information of the second sterilization device indication device INDD2, image information of the first instrument indication device INDT1, and image information of the second instrument indication device INDT2, and transmit the image information of the first sterilization device indication device INDD1, the image information of the first instrument indication device INDT1, the image information of the second sterilization device indication device INDD2, and the image information of the second instrument indication device INDT2 to the server 11 for storage, recording, and analysis.

Further, the user may also use the image capturing module 131 of the mobile device 13 to capture image information of the first sterilization device indication label LABD1, image information of the second sterilization device indication label LABD2, image information of the first instrument indication label LABT1, and image information of the second instrument indication label LABT2, and transmit the image information of the first sterilization device indication label LABD1, the image information of the first instrument indication label LABT1, and the image information of the second instrument indication label LABT2 to the server 11 for storage, recording, and analysis.

In other embodiments, the user may transmit only the image information of the first sterilization device indication device INDD1, the image information of the first instrument indication device INDT1, and the image information of the second instrument indication device INDT2 to the server 11 for storage, recording, and analysis.

In steps S140 and S150, after placing the plurality of instrument packages TP in the sterilization device 12, the user may select different sterilization procedures for the sterilization device 12 according to different types of instruments. In addition, the user may also use the image capturing module 131 of the mobile device 13 to capture display information regarding the sterilization procedures of the sterilization device 12, and transmit the display information to the server 11 for storage and recording.

In steps S160 and S170, after the sterilization device 12 completes the sterilization procedure, the user opens the sterilization device 12 to take out the plurality of instrument packages TP subjected to the sterilization procedure.

In this case, the user may use the image capturing module 131 of the mobile device 13 to capture image information of the first sterilization device indication device INDD1 subjected to the sterilization procedure, image information of the second sterilization device indication device INDD2 subjected to the sterilization procedure, image information of the second instrument indication device INDT2 which is disposed outside the instrument package TP and subjected to the sterilization procedure, and image information of the second instrument indication label LABT2 which is disposed outside the instrument package TP and subjected to the sterilization procedure, and transmit the image information of the first sterilization device indication device, the second sterilization device indication device, the second instrument indication device, and the second instrument indication label that are subjected to the sterilization procedure to the server 11.

Afterwards, the server 11 determines, according to the image information of the second instrument indication device, the second instrument indication label, the first sterilization device indication device, and the first sterilization device indication label that are subjected to the sterilization procedure, whether or not the instrument TOOL to be sterilized meets a sterilization standard. That is, the server 11 performs an image recognition procedure on the image information of the second instrument indication device and the second instrument indication label that are subjected to the sterilization procedure, to determine whether or not a sterilization indication area on the second instrument indication device INDT2 disposed outside the instrument package TP meets a fourth sterilization standard after the sterilization procedure. The server 11 performs image recognition on the image information of the first sterilization device indication device subjected to the sterilization procedure. The server recognizes information of an elongated bottle-shaped object in the image information of the first sterilization device indication device subjected to the sterilization procedure, and further analyzes color information of a first indication area in the information of the elongated bottle-shaped object. The image information of the first sterilization device indication label, the image information of the first instrument indication label, and the image information of the second instrument indication label may be a one-dimensional bar code, a two-dimensional bar code, a multi-dimensional bar code, or an RFID. The image information of the first sterilization device indication label, the image information of the first instrument indication label, and the image information of the second instrument indication label are mainly serial numbers or running numbers after decoding, so as to be associated with the image information of the first sterilization device indication device, the image information of the first instrument indication device, and the image information of the second instrument indication device before and after sterilization, and to be recorded.

The server 11 also performs image recognition on the image information of the second sterilization device indication device subjected to the sterilization procedure. First, the server 11 analyzes a second indication area IDA2 in the image information of the second sterilization device indication device. The server 11 determines, according to color information and length information of the second indication area IDA2 in the image information of the second sterilization device indication device, whether or not a sterilization environment in the sterilization device 12 meets a sterilization standard. A color zone in the second indication area IDA2 includes a first color and a second color. Before the sterilization procedure, the first color of the second indication area IDA2 has a first length D1. After the sterilization procedure, a color of a portion of the second indication area IDA2 is changed from the first color to the second color. In this embodiment, the first color is white, and the second color is black. After the sterilization procedure, the first color has a second length D2, and the second color has a third length D3. A sum of the second length D2 and the third length D3 equals to the first length D1. Only when the third length D3 is greater than the second length D2, does the sterilization environment in the sterilization device 12 meets the sterilization standard. That is, if the third length D3 exceeds a reference line REF, the first instrument indication device INDT1 meets a third sterilization standard. If the third length D3 does not exceed the reference line REF, the second sterilization device indication device INDD2 fails to meet a second sterilization standard. As shown in FIGS. 3B, 3C, and 3D, the instrument package TP meets the sterilization standard. However, as shown in both FIGS. 3E and 3F, the instrument package TP fails to meet the sterilization standard.

The server 11 also performs an image recognition procedure on the image information of the second instrument indication device and the second instrument indication label that are subjected to the sterilization procedure. A plurality of diagonal stripes is provided on a surface of the second instrument indication device INDT2. When the instrument package TP meets the fourth sterilization standard after the sterilization procedure, the plurality of diagonal stripes on the second instrument indication device INDT2 changes in color.

The instrument sterilization monitoring method further includes the following steps:

After the instrument package TP subjected to the sterilization procedure is unpacked, image information of the first instrument indication device subjected to the sterilization procedure is captured and transmitted to the server (step S180).

The server determines, according to the image information of the first instrument indication device subjected to the sterilization procedure, whether or not the instruments TOOL in the instrument package TP meet a third sterilization standard (step S190).

In steps S180 and S190, after the instrument package TP subjected to the sterilization procedure is unpacked, the user uses the image capturing module 131 of the mobile device 13 to capture image information of the first instrument indication device INDT1 subjected to the sterilization procedure and image information of the first instrument indication label LABT1 subjected to the sterilization procedure, and transmits the image information of the first instrument indication device INDT1 and the first instrument indication label LABT1 that are subjected to the sterilization procedure to the server 11.

The server 11 performs image recognition on the image information of the first instrument indication device and the image information of the first instrument indication label, to determine whether or not the instruments TOOL in the instrument package TP meet a third sterilization standard after the sterilization procedure.

In this embodiment, the first sterilization device indication device INDD1, the second sterilization device indication device INDD2, the first instrument indication device INDT1, and the second instrument indication device INDT2 respectively include a first sterilization device indication area IDA1, a second sterilization device indication area IDA2, a first instrument indication area ITA1, and a second instrument indication area ITA2.

The server 11 determines, according to color change information of the first sterilization device indication area IDA1 in the image information of the first sterilization device indication device, whether or not the sterilization device 12 meets a first sterilization standard. The server 11 determines, according to color change and length change information of the second sterilization device indication area IDA2 in the image information of the second sterilization device indication device, whether or not the sterilization environment in the sterilization device 12 meets a second sterilization standard.

The server 11 also analyzes and recognizes the image information of the first instrument indication device, and the first instrument indication area ITA1 of the first instrument indication device INDT1 defines an indicator coating range. Before the sterilization procedure, a color of the first instrument indication area ITA1 is white (as shown in FIG. 4A), after the sterilization procedure, the color of the first instrument indication area ITA1 is changed to black (as shown in FIG. 4B). The first instrument indication area ITA1 has a total length of D6. After the sterilization procedure, if sterilization succeeds, a black color emerges in the first instrument indication area ITA1, and moreover extends to the total length D6. Only in this case, the first instrument indication device INDT1 meets the third sterilization standard. In addition, if a length of black segments shown in FIGS. 4C, 4D, 4E, 4F, and 4G are all shorter than the total length D6 of the first instrument indication area ITA1, or the black color is presented segmentally, the first instrument indication device INDT1 fails to meet the third sterilization standard in either of the two cases. Alternatively, as shown in FIG. 4H, although the first instrument indication area ITA1 has a color change, the color is neither black nor dark gray. In this case, the first instrument indication device INDT1 also fails to meet the third sterilization standard.

The server 11 determines, according to a color change of the second instrument indication area ITA2 of the second instrument indication device INDT2, whether or not the instrument package TP meets a fourth sterilization standard.

The server 11 determines, according to color information and length information of the first instrument indication area ITA1 in the image information of the first instrument indication device, whether or not the instruments TOOL to be sterilized in the instrument package TP meet a third sterilization standard. Moreover, when the user uploads all the image information to the server 11 by using the application program in the mobile device 13, the server 11 may record upload times of all the image information and GPS position information of the mobile device 13, further analyze time information of metadata of each piece of image information, and compare the analyzed time information with the upload time, so as to guarantee that capturing time of the image information is close to the upload time. In addition, the server 11 may monitor instrument use by the user according to a time interval during which the sterilization device 12 performs the sterilization procedure each time, and according to the quantity of the instrument packages TP and a related record (from the second instrument indication label outside a package). Further, when the server 11 recognizes the first instrument indication area ITA1 of the first instrument indication device INDT1, a length of a color change zone in the first instrument indication area ITA1 is necessarily equal to the total length D6, and a color variation of the first instrument indication area ITA1 is necessarily less than a preset grayscale value. For example, based on a 256-level grayscale chart (0 to 255), a grayscale value of the first instrument indication area ITA1 may be set to be less than or equal to a 50 grayscale value, so that the third sterilization standard can be met. Moreover, if it is determined that the preset grayscale value at which the third sterilization standard can be reached is excessively large, a deviation from an actual sterilization status easily occurs.

A color zone in the second instrument indication area ITA2 includes a first color and a second color. After the sterilization procedure, the second instrument indication area ITA2 changes from the first color to the second color.

In this embodiment, when the first sterilization device indication device INDD1 fails to meet the first sterilization standard or the second sterilization device indication device INDD2 fails to meet the second sterilization standard, all the instrument packages TP after the current sterilization procedure are required to be subjected to the sterilization procedure again, and it is unsuitable to use any of the instrument packages TP after the current sterilization procedure. When the second instrument indication device INDT2 disposed outside the instrument package TP fails to meet the fourth sterilization standard, the instruments TOOL in the instrument package TP are required to be re-packaged and subjected to another sterilization procedure. Likewise, when the first instrument indication device INDT1 fails to meet the third sterilization standard after the instrument package TP is unpacked, the instruments TOOL in the instrument package TP cannot be used, and are required to be re-packaged and subjected to another sterilization procedure.

Advantageous Effects of the Embodiments

One of advantageous effects achieved by the present disclosure lies in that the instrument sterilization monitoring system and method provided by the present disclosure reduce the workload of medical staff. It is only required to use a common mobile phone to photograph and upload instrument packages, and indicators and labels before and after sterilization, thus easily monitoring whether or not sterilization for instrument packages in each sterilization procedure succeeds. The instrument sterilization monitoring system and method provided by the present disclosure can further associate the instrument package with patients using the instruments, greatly improving the safety of medical care. Moreover, the instrument sterilization monitoring system and method provided by the present disclosure records information about instruments, an instrument combination, a sterilization device, the sterilization procedure, etc., and their mutual correlations via the Internet of things and further uploads recorded data to a blockchain platform, so that the data cannot be altered, thus facilitating checking, judgment, and status tracking in the future.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An instrument sterilization monitoring system, comprising:
   a server; and
   a sterilization device being used to perform a sterilization procedure on a plurality of instruments to be sterilized;
   wherein a mobile device including an image capturing module is used by a user to log in to the server; and
   the server determines, according to image information of a plurality of sterilization device indication devices of the sterilization device and image information of a plurality of instrument indication devices of the instruments to be sterilized, whether or not the sterilization device and the instruments to be sterilized reach a plurality of sterilization standards;
   wherein a first sterilization device indication device and a second sterilization device indication device are disposed in the sterilization device; at least one of the instruments to be sterilized and a first instrument indication device are placed together in a packaging material, to form an instrument package; a second instrument indication device is disposed outside the instrument package; the plurality of instruments to be sterilized is packaged to form a plurality of instrument packages, and the plurality of instrument packages are placed in the sterilization device to perform the sterilization procedure; the first sterilization device indication device includes a first sterilization device indication label, each of the second sterilization device indication devices includes a second sterilization device indication label, each of the first instrument indication devices includes a first instrument indication label, and each of the second instrument indication devices includes a second instrument indication label;
   the image capturing module of the mobile device is used to capture image information of the first sterilization device indication device and image information of the corresponding first sterilization device indication label, and transmits the image information of the first sterilization device indication device and the image information of the first sterilization device indication label to the server; then, when packaging the first instrument indication devices and the instruments to be sterilized, the image information of the first instrument indication devices corresponding to the plurality of instruments to be sterilized and image information of the first instrument indication labels, and transmits the image information of the first instrument indication devices and the image information of the first instrument indication labels are captured to the server; and afterwards, the image capturing module of the mobile device is used to capture image information of the second instrument indication devices respectively on the plurality of instrument packages and image information of the corresponding second instrument indication labels, and transmits the image information of each of the second instrument indication devices and the image information of each of the second instrument indication labels to the server,
   wherein after the sterilization device completes the sterilization procedure, image information of the second instrument indication device subjected to the sterilization procedure and image information of the second instrument indication label subjected to the sterilization procedure are captured; and transmits the image information of the second instrument indication device and the second instrument indication label that are subjected to the sterilization procedure to the server,
   wherein the image capturing module of the mobile device is used to capture image information of the first sterilization device indication device subjected to the sterilization procedure, image information of the second sterilization device indication device subjected to the sterilization procedure, image information of the first sterilization device indication label subjected to the sterilization procedure, and image information of the second sterilization device indication label subjected to the sterilization procedure, and transmits the image information of the first sterilization device indication device, the second sterilization device indication device, the first sterilization device indication label, and the second sterilization device indication label that are subjected to the sterilization procedure to the server,
   wherein the server determines, according to the image information of the second instrument indication device, the second instrument indication label, the first sterilization device indication device, the first sterilization device indication label, and the second sterilization device indication label that are subjected to the sterilization procedure, whether or not the instruments to be sterilized meet a sterilization standard.

2. The instrument sterilization monitoring system of claim 1, wherein the server determines, according to color change information of a first indication area in the image information of the first sterilization device indication device, whether or not the sterilization device meets a first sterilization standard; and determines, according to a second indication area in the image information of the second sterilization device indication device, whether or not the sterilization device meets a second sterilization standard.

3. The instrument sterilization monitoring system of claim 2, wherein after the instrument package subjected to the sterilization procedure is unpacked, the image capturing module of the mobile device is used to capture image information of the first instrument indication device subjected to the sterilization procedure and image information of the first instrument indication label subjected to the sterilization procedure; and transmits the image information of the first instrument indication device and the first instrument indication label that are subjected to the sterilization procedure to the server; and the server determines, according to the image information of the first instrument indication device and the image information of the first instrument indication label, whether or not the instrument package subjected to the sterilization procedure meets a third sterilization standard.

4. The instrument sterilization monitoring system of claim 3, wherein the server determines, according to color change information of a third indication area in the second instrument indication device, whether or not the instrument package meets a fourth sterilization standard.

5. The instrument sterilization monitoring system of claim 4, wherein the server determines, according to first length information of a first color and second length information of a second color of a third indication area in the image information of the first instrument indication device, whether or not the instruments to be sterilized in the instrument package meet the third sterilization standard.

6. The instrument sterilization monitoring system of claim 1, wherein the mobile device is a smart phone, a tablet computer, or a wearable electronic device.

7. An instrument sterilization monitoring system, comprising:
　a server; and
　a sterilization device being used to perform a sterilization procedure on a predetermined quantity of instruments to be sterilized;
　wherein a mobile device including an image capturing module is used by a user to log in to the server by a user account and a user password;
　wherein a first sterilization device indication device and a second sterilization device indication device are disposed in the sterilization device; at least one of the instruments to be sterilized and a first instrument indication device are placed together in a packaging material to form an instrument package; a second instrument indication device is disposed outside the instrument package; the plurality of instruments to be sterilized is packaged to form a plurality of instrument packages, and the plurality of instrument packages are placed in the sterilization device to perform the sterilization procedure; the image capturing module of the mobile device is used to capture image information of the first sterilization device indication device and image information of the second sterilization device indication device, and the image information of the first sterilization device indication device and the image information of the second sterilization device indication device are transmitted to the server; then, when packaging the first instrument indication device and the instruments to be sterilized, image information of the first instrument indication devices corresponding to the plurality of instruments to be sterilized is captured, and the image information of the first instrument indication device is transmitted to the server; the image capturing module of the mobile device is used to capture image information of the second instrument indication device disposed outside each instrument package, and the image information of the second instrument indication device is transmitted to the server;
　wherein after the sterilization device completes the sterilization procedure, image information of the second instrument indication device subjected to the sterilization procedure is captured, and the image information of the second instrument indication device subjected to the sterilization procedure is transmitted to the server;
　wherein the image capturing module of the mobile device is used to capture image information of the first sterilization device indication device subjected to the sterilization procedure and image information of the second sterilization device indication device subjected to the sterilization procedure; and the image information of the first sterilization device indication device and the second sterilization device indication device that are subjected to the sterilization procedure is transmitted to the server;
　wherein the server determines, according to the image information of the second instrument indication device, the first sterilization device indication device, and the second sterilization device indication device that are subjected to the sterilization procedure, whether or not the instruments to be sterilized meet a sterilization standard.

* * * * *